(12) United States Patent
Nink et al.

(10) Patent No.: US 10,732,162 B2
(45) Date of Patent: Aug. 4, 2020

(54) METHOD AND DEVICE FOR DETERMINING THE DISINTEGRATION TIME OF FILM-SHAPED PHARMACEUTICAL DOSAGE FORMS

(71) Applicant: HEXAL AG, Holzkirchen (DE)

(72) Inventors: Jörg Nink, Holzkirchen (DE); Josef Pichler, Holzkirchen (DE); Katharina Obermüller, Holzkirchen (DE); Alexander Wotzko, Holzkirchen (DE)

(73) Assignee: Hexal AG, Holzkirchen (DE)

( * ) Notice: Subject to any disclaimer, the term of this patent is extended or adjusted under 35 U.S.C. 154(b) by 326 days.

(21) Appl. No.: 15/501,064

(22) PCT Filed: Aug. 5, 2015

(86) PCT No.: PCT/EP2015/068057
§ 371 (c)(1),
(2) Date: Feb. 1, 2017

(87) PCT Pub. No.: WO2016/020438
PCT Pub. Date: Feb. 11, 2016

(65) Prior Publication Data
US 2017/0254791 A1  Sep. 7, 2017

(30) Foreign Application Priority Data
Aug. 6, 2014  (EP) ..................................... 14180060

(51) Int. Cl.
*G01N 33/15* (2006.01)
*G01N 13/00* (2006.01)
(Continued)

(52) U.S. Cl.
CPC ............. *G01N 33/15* (2013.01); *G01N 1/286* (2013.01); *G01N 13/00* (2013.01);
(Continued)

(58) Field of Classification Search
CPC ........ G01N 33/15; G01N 1/286; G01N 13/00; G01N 2013/0266; G01N 2013/0241; G01N 2013/006
(Continued)

(56) References Cited

U.S. PATENT DOCUMENTS 3,684,448 A * 8/1972 Stricker ................ G01N 13/00
422/68.1
4,335,438 A * 6/1982 Smolen ................. G01N 13/00
422/81
(Continued)

FOREIGN PATENT DOCUMENTS

DE         9419245 U1    1/1995
DE     102005049220 A1   4/2007
(Continued)

OTHER PUBLICATIONS

Garsuch et al. Novel analytical methods for the characterization of oral wafers, European Jornal of Pharmaceutics and Biopharmaceutics, 73 (2009) 195-201 (Year: 2009).*
(Continued)

*Primary Examiner* — Marrit Eyassu
(74) *Attorney, Agent, or Firm* — United IP Counselors, LLC

(57) ABSTRACT

The present invention relates to a method for determining the disintegration time of a film-shaped pharmaceutical dosage form and a disintegration testing device for use in such a method.

15 Claims, 8 Drawing Sheets

(51) Int. Cl.
*G01N 1/28* (2006.01)
*G01N 13/02* (2006.01)

(52) U.S. Cl.
CPC .............. *G01N 2013/006* (2013.01); *G01N 2013/0241* (2013.01); *G01N 2013/0266* (2013.01)

(58) Field of Classification Search
USPC ....................................................... 73/1.02
See application file for complete search history.

(56) References Cited

U.S. PATENT DOCUMENTS

| | | | | |
|---|---|---|---|---|
| 4,594,884 | A * | 6/1986 | Bondi | G01N 13/00 210/321.84 |
| 5,198,109 | A * | 3/1993 | Hanson | G01N 13/00 210/321.75 |
| 5,296,139 | A * | 3/1994 | Hanson | B01D 61/28 210/297 |
| 5,490,415 | A * | 2/1996 | Mak | G01N 13/00 210/321.84 |
| 6,294,134 | B1 * | 9/2001 | Schenk | G01N 13/00 422/559 |
| 6,360,588 | B1 * | 3/2002 | Ross | G01N 13/04 73/38 |
| 7,635,452 | B2 * | 12/2009 | Roscoe | B01L 3/5025 422/50 |
| 2005/0003550 | A1 | 1/2005 | Kyne | G01N 33/15 436/2 |
| 2007/0202057 | A1 | 8/2007 | Fankhauser et al. | |
| 2007/0218115 | A1 | 9/2007 | Bott et al. | |
| 2008/0223116 | A1 * | 9/2008 | Alkhawam | G01N 13/00 73/64.56 |
| 2009/0064768 | A1 * | 3/2009 | Alkhawam | G01N 13/00 73/64.56 |
| 2012/0279324 | A1 * | 11/2012 | Minekus | G09B 23/12 73/866.4 |
| 2013/0330397 | A1 * | 12/2013 | Neas | A61L 26/0066 424/445 |
| 2014/0305225 | A1 * | 10/2014 | Heng | G01N 13/00 73/841 |

FOREIGN PATENT DOCUMENTS

| | | |
|---|---|---|
| EP | 0975949 A1 | 2/2000 |
| EP | 2263662 A1 | 12/2010 |
| EP | 2732813 A1 | 5/2014 |
| JP | 2008032482 A | 2/2008 |
| WO | 9857144 A1 | 12/1998 |
| WO | 2007086470 A1 | 8/2007 |
| WO | 2009128433 A1 | 10/2009 |
| WO | 2010094341 A1 | 8/2010 |

OTHER PUBLICATIONS

International Search Report dated Oct. 19, 2015 for corresponding foreign Application No. PCT/EP2015/068057, 3 pp.
Garsuch et al.,"Novel analytical methods for the characterization or oral wafers", European Journal of Pharmaceutics and Biopharmaceutics, Elsevier Science Publishers B.V., vol. 73, No. 1, May 29, 2009, pp. 195-201.
Office Action issued in Eurasian Patent Application No. 201692432/28 dated Apr. 20, 2018, 9 pages.
Office Action issued in Eurasian Patent Application No. 201692432/28 dated Oct. 11, 2018, 6 pages.
Notification for Reasons for Rejection issued in Japanese Patent Application No. 2016-575904, dated Jan. 15, 2018, 6 pages
Notification for Reasons for Refusal issued in Japanese Patent Application No. 2016-575904, dated Aug. 23, 2018, 3 pages.
Final Office Action issued in Korean Patent Application No. 10-2017-7001129, dated Feb. 13, 2019, 5 pages.
Office Action issued in Korean Patent Application No. 10-2017-7001129, dated Sep. 17, 2018, 9 pages.
Office Action issued in Eurasian Patent Application No. 201692432/28, dated May 23, 2019 with English Translation.
Murata, Y., et al., Preparation of Fast Dissolving Films for Oral Dosage from Natural Polysaccharides, Materials 2010, vol. 3, p. 4291-4299.

* cited by examiner

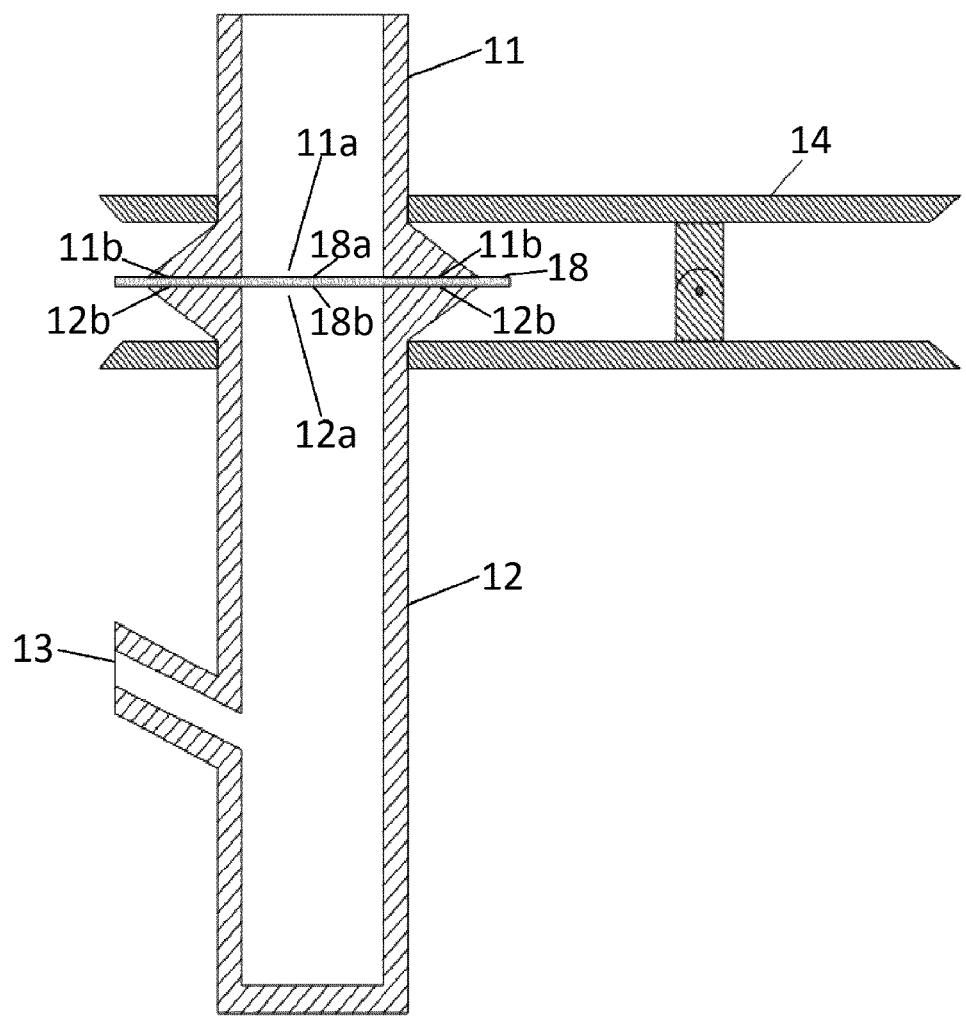

METHOD AND DEVICE FOR DETERMINING THE DISINTEGRATION TIME OF FILM-SHAPED PHARMACEUTICAL DOSAGE FORMS

CROSS-REFERENCE TO RELATED APPLICATIONS

This application is the U.S. National Phase of PCT International Application No. PCT/EP2015/068057, filed on Aug. 5, 2015. That application claims priority to European Patent Application No. 14180060.7, filed Aug. 6, 2014. The contents of both applications are herein incorporated by reference in their entirety.

The present invention relates to a method and a device for determining the disintegration time of film-shaped pharmaceutical dosage forms.

The determination of the disintegration time of pharmaceutical dosage forms is of importance as a critical quality control and performance test in the pharmaceutical industry.

The disintegration time of a pharmaceutical dosage form is one parameter which influences the in vivo performance of that pharmaceutical dosage form. Therefore, the availability of at least one accurate and reproducible analytical test to evaluate the disintegration behavior of any pharmaceutical dosage form is essential.

Disintegration is defined in the European Pharmacopeia (Ph. Eur. 8.0; Chapter 2.9.1) for tablets and capsules as that state in which any residue of the unit (except fragments of insoluble coating or capsule shell) remaining on the screen of the test apparatus or adhering to the lower surface of the discs, if used, is a soft mass having no palpably firm core. For suppositories and pessaries, the European Pharmacopeia (Ph. Eur. 8.0; Chapter 2.9.2) considers disintegration to be achieved when
a) dissolution is complete,
b) the components of the suppository or pessary have separated: melted fatty substances collect on the surface of the liquid, insoluble powders fall to the bottom and soluble components dissolve, depending on the type of preparation, the components may be distributed in one or more of these ways,
c) there is softening of the sample that may be accompanied by appreciable change of shape without complete separation of the components, the softening is such that the suppository or pessary no longer has a solid core offering resistance to pressure of a glass rod,
d) rupture of the gelatin shell of rectal or vaginal capsules occurs allowing release of the contents,
e) no residue remains on the perforated disc or if a residue remains, it consists only of a soft or frothy mass having no solid core offering resistance to pressure of a glass rod (vaginal tablets).

The European Pharmacopeia (Ph. Eur. 8.0) does not specify when disintegration of pharmaceutical dosage forms other than the above mentioned tablets, capsules, suppositories and pessaries is considered to be achieved. In particular, disintegration of film-shaped pharmaceutical dosage forms is not addressed in the European Pharmacopeia. The same holds true for the US Pharmacopeia (USP 36).

The European Pharmacopeia (Ph. Eur. 8.0; Chapter 2.9.1) and the US Pharmacopoeia (USP 36 <701>) define methods and devices for determining the disintegration time of tablets, capsules, suppositories and pessaries. However, methods and devices for determining the disintegration time of film-shaped pharmaceutical dosage forms, such as orodispersible films, are not described. Moreover, the methods and devices as described in the European and US Pharmacopeia for certain pharmaceutical dosage forms cannot suitably be used for determining the disintegration time of such film-shaped pharmaceutical dosage forms. For example, the film-shaped pharmaceutical dosage forms tend to stick to the device and/or the dosage forms or parts thereof stay on the surface of the disintegration liquid which makes an assessment of the disintegration inaccurate and irreproducible. Moreover, the methods according to the European and US Pharmacopeia use a rather large amount of disintegration liquid. This is not always in accordance with the conditions in a natural environment, for example when the film-shaped pharmaceutical dosage form is intended to disintegrate in the oral cavity where the amount of liquid available for disintegration is rather small.

In addition to the methods and devices described in the European and US Pharmacopeia, improved devices and methods based thereon and alternative devices and methods are known from the prior art as summarized below:

DE 94 19 245 U1 describes an automatic measurement device for measuring the disintegration time of tablets and coated tablets.

EP 0 975 949 A describes a device for determining the decay time of compressed medicaments such as tablets and capsules, and a corresponding method.

WO 98/57144 A1 describes a device for determining the decay time of compressed medicinal shaped bodies (e.g. tablets and capsules) and a corresponding method.

DE 10 2005 049 220 A describes a method and a device for measuring the disintegration time of solid samples, in particular tablets and suppositories, in liquids.

JP 2008032482 A is directed at a tablet disintegration test method and a disintegration tester for measuring the disintegration time of a tablet, in particular an intraorally disintegrating tablet.

WO2007/08470 A1 describes a device for testing tablet disintegrating in the oral cavity.

WO 2010/094341 A1 describes a decay time measurement device for automatically determining the decay time of solid substance samples.

In the absence of suitable methods for determining the disintegration time of film-shaped pharmaceutical dosage forms, the present inventors previously used the following method: A Petri dish was filled with a small amount of the disintegration medium and the film-shaped pharmaceutical dosage form was placed onto the surface of the disintegration medium. The disintegration of the film-shaped pharmaceutical dosage form was then observed visually. Usually, the film-shaped pharmaceutical dosage form starts to disintegrate at one of the edges, becomes porous, the porous structure falls apart and then the single parts become smaller and move away from each other. Alternatively, the film-shaped pharmaceutical dosage form divides into two or more bigger parts, one of which stays at the surface of the disintegration medium, the other one sinks down and starts to disintegrate while the one being at the surface stays intact considerably longer. In view of this, even for one and the same person determining disintegration, it is very difficult to define the correct end-point for measuring the disintegration time of a sample. If several persons determine the end-point, the variation will be even greater. The differences in the disintegration time for the same sample can be more than 30 seconds for one and the same person and even more than 1 minute if different persons are involved. This difference is not acceptable for measuring disintegration times which may be as short as a few minutes and in some cases are even shorter than 1 minute.

The method using a Petri dish is additionally associated with the disadvantage that only one surface of the film-shaped pharmaceutical dosage form can be observed during disintegration testing. Observing the upper and the lower surface may, however, be important in the process of optimizing film-shaped pharmaceutical dosage forms with regard to their disintegration behavior.

In view of the above, there is the need for an accurate and reproducible, easy-to-use disintegration testing method and a corresponding device providing a clearly defined end-point and low variability. In particular, the method and device should be suitable as a standard method and device for determining the disintegration time of film-shaped pharmaceutical dosage forms, such as orodispersible films.

The present invention provides an advantageous method for determining the disintegration time of film-shaped pharmaceutical dosage forms, for example, orodispersible films, which method is characterized by a clearly defined end-point, is highly accurate and reproducible, is easy to use and standardize, can be advantageously used in the development and optimization of film-shaped pharmaceutical dosage forms, and wherein the amount of the disintegration liquid can be selected over a wide range, and wherein the disadvantages of the known methods, such as the sticking of the dosage form at the device or the floating of the dosage form onto the surface of the disintegration medium are avoided. Additionally, the present invention provides a device for carrying out the method of the present invention.

According to a first aspect, the present invention relates to a method for determining the disintegration time of a film-shaped pharmaceutical dosage form comprising:
(a) placing the film-shaped pharmaceutical dosage form between a bottom side opening of an upper liquid receiving section and a top side opening of a lower liquid receiving section;
(b) applying a liquid into the upper liquid receiving section;
(c) observing the penetration of the liquid through the film-shaped pharmaceutical dosage form; and
(d) determining the time between step (b) and step (c).

According to a second aspect, the present invention relates to a disintegration testing device comprising
(i) an upper liquid receiving section having a bottom side opening, and
(ii) a lower liquid receiving section having a top side opening, wherein the bottom side opening of the upper liquid receiving section and the top side opening of the lower liquid receiving section are formed so as to hold a film-shaped pharmaceutical dosage form between the upper liquid receiving section and the lower liquid receiving section.

According to a third aspect, the present invention relates to the use of a device comprising
(i) an upper liquid receiving section having a bottom side opening, and
(ii) a lower liquid receiving section having a top side opening, wherein the bottom side opening of the upper liquid receiving section and the top side opening of the lower liquid receiving section are formed so as to hold a film-shaped pharmaceutical dosage form (preferably an orodispersible film) between the upper liquid receiving section and the lower liquid receiving section
for determining the disintegration time of the film-shaped pharmaceutical dosage form.

Before the present invention is described in detail below, it is to be understood that this invention is not limited to the particular methodology, protocols and reagents described herein, as these may vary. It is also to be understood that the terminology used herein is for the purpose of describing particular aspects and embodiments of the invention only, and is not intended to limit the scope of the present invention which will be limited only by the appended claims. Unless defined otherwise, all technical and scientific terms used herein have the same meanings as commonly understood by one of ordinary skill in the art.

Throughout this specification and the claims which follow, unless the context requires otherwise, the word "comprise", and variations such as "comprises" and "comprising", will be understood to imply the inclusion of a stated integer or step or group of integers or steps, but not the exclusion of any other integer or step or group of integers or steps.

Several documents are cited throughout the text of this specification. Each of the documents cited herein, whether supra or infra, is hereby incorporated by reference in its entirety.

In the following, definitions of the terms used herein are provided. In each instance of their use in this specification, these terms will have the respectively defined meaning and preferred meanings.

The terms pharmaceutical dosage form, pharmaceutical preparation, pharmaceutical formulation and medicament are used interchangeably herein and mean any product comprising an active pharmaceutical ingredient (API).

The term film-shaped pharmaceutical dosage form comprises thin films (also referred to as "wafers", "strips" or "discs"), for example films having a thickness of 50 to 2000 µm, in particular films having a thickness of 50 to 2000 µm and having two planar surfaces, but also comprises dosage forms having a thickness of more than 2000 µm and two convex surfaces (such as oval or oblong tablets, in particular orally dispersible tablets) or one planar and one convex surface or having irregular surfaces (such as pellets) as long as their disintegration time can be determined with the disintegration device or by the disintegration method of the present invention. The film-shaped pharmaceutical dosage form can, for example, be a flexible or non-flexible sheet of material (the material comprising, for example, at least one polymer) having a thickness of 50 to 2000 µm.

The film-shaped pharmaceutical dosage forms can be administered in an oral, mucosal, buccal, top-lingual, sub-lingual, topical, vaginal or rectal way.

The film-shaped pharmaceutical dosage forms of the present invention comprise orodispersible films (also referred to as orally disintegrating films). Orodispersible films disintegrate within the oral cavity and allow for absorption of the API though the oral mucosa or for absorption through the gastrointestinal tract after the disintegrated film components have been swallowed.

Usually such orodispersible films are prepared by using hydrophilic polymers that dissolve in the oral cavity rapidly (usually within 5 seconds to 10 minutes), for example on or under the tongue (top-lingual or sub-lingual) or in the buccal cavity.

The film-shaped pharmaceutical dosage forms of the present invention comprise one API or a mixture of two or more APIs and suitable excipients. The excipients can include any pharmaceutical acceptable additives such as stabilizers, diluents, binders, thickeners or granulating agents, glidants (flow aids) and lubricants to ensure efficient manufacturing; disintegrants to promote disintegration in the digestive tract comprising the oral cavity; plasticizers for improving the mechanical properties; sweeteners or flavours to enhance taste; and pigments to make the dosage forms visually attractive.

The term "pharmaceutically acceptable" means approved by a regulatory authority of the European Union or one of its member states or an agency of the federal or a state government of the USA or listed in the EU or US Pharmacopeia or other generally recognized pharmacopeia for use in animals, and more particularly in humans.

"Disintegration" and "disintegration time" are used interchangeably and are defined for the method of the present invention as the point in time when the liquid (the disintegration medium) penetrates through the pharmaceutical dosage form. More specifically, in the sense of the invention, the disintegration time is defined by the time between step b) and step c) or the time from application of the liquid into the upper liquid receiving section and detachment and fall of a first droplet from the bottom surface of the pharmaceutical dosage form.

For methods other than the method of the present invention, "disintegration" and "disintegration time" are defined herein as the complete decomposition of the film-shaped pharmaceutical dosage form into its primary particles. It is worth noting that disintegration is to be distinguished from dissolution. Dissolution refers to the active pharmaceutical ingredient (API) which is present in a pharmaceutical dosage form and is influenced by the disintegration of the pharmaceutical dosage form and by the solubility of the active pharmaceutical ingredient in the given medium.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The method for determining the disintegration time of a film-shaped pharmaceutical dosage form according to the first aspect of the present invention comprises:
(a) placing the pharmaceutical dosage form between a bottom side opening of an upper liquid receiving section and a top side opening of a lower liquid receiving section;
(b) applying a liquid into the upper liquid receiving section;
(c) observing the penetration of the liquid through the film-shaped pharmaceutical dosage form;
(d) determining the time between step (b) and step (c).

The pharmaceutical dosage form is preferably an orodispersible film.

In the method of the invention, the upper liquid receiving section and the pharmaceutical dosage form are tightly attached so as to form a liquid receptacle.

The liquid is preferably selected from either water or an artificial body fluid. The term "artificial body fluid" means a liquid which comprises an aqueous solution of one or more components of body fluids of the human or animal body like saliva, gastric juice or gut juice. Preferably, the artificial body fluid is selected from artificial saliva, artificial gastric juice and/or artificial gut juice.

The amount of liquid applied into the upper liquid receiving section and thus onto the upper side of the film-shaped pharmaceutical dosage form is preferably adapted to the size of the pharmaceutical dosage form to be tested. By way of example, 250 µl of liquid may be applied into the upper liquid receiving section for testing a film-shaped pharmaceutical dosage form having a surface area of 1 cm$^2$ and a thickness of 150 µm. The appropriate amount of liquid for a film-shaped particular dosage form can be easily determined by an average person skilled in the art.

The liquid can be applied manually, for example by using a pipette or a container having a valve, preferably using a pipette, or by a semi-automatic or automatic device, for example, a pump, an electromagnetic shutter device or an automated liquid handling device, such as an automated liquid handling device which is commercially available, for example, from Eppendorf or Hamilton Robotics.

The penetration of the liquid through the pharmaceutical dosage form is preferably observed by detecting a liquid drain through the pharmaceutical dosage form from the surface constituting the bottom of the upper liquid receiving section to the surface constituting the top cover of the lower liquid receiving section. More preferably, the penetration of the liquid through the pharmaceutical dosage form is detected by observing the detachment of a first droplet from the pharmaceutical dosage form placed between the bottom side opening of the upper liquid receiving section and the top side opening of the lower liquid receiving section.

The penetration of the liquid through the pharmaceutical dosage form can be detected visually. The penetration of the liquid through the pharmaceutical dosage form can alternatively be detected by a detecting means selected, for example, from one or more of: a weight change sensor (preferably an electronic balance), an impact sensor, an image recognition sensor (preferably a photo sensor), a capacitive sensor, an electric resistivity sensor, a motion sensor, a vibration sensor, and an acoustic sensor.

The time between step (b) and step (c) can be measured manually, preferably using a stopwatch. The time between step (b) and step (c) can alternatively be measured automatically with a time measurement means. The time measurement means is preferably coupled to the liquid delivery means which applies the liquid into the upper liquid receiving section. In another preferred aspect of the invention, the time measurement means is coupled to a detecting means which detects the penetration of the liquid through the pharmaceutical dosage form. In a particularly preferred aspect, the time between step (b) and step (c) is measured by a time measurement means which is coupled to a liquid delivery means which applies the liquid into the upper liquid receiving section and a detecting means which detects the penetration of the liquid through the pharmaceutical dosage form.

The temperature of the liquid applied into the upper liquid receiving section can be in the range of from 15 to 40° C., preferably in the range of from 15 to 25° C., more preferably 20 to 25° C. In an alternative preferred aspect, the temperature of the liquid applied into the upper liquid receiving section can be in the range of from 30 to 40° C., more preferably 32° C.±2° C. or 37° C.±2° C.

In a further preferred aspect, the method of the present invention additionally comprises the step of
(e) removing the liquid from the lower liquid receiving section.

In an even more preferred aspect, the method of the present invention additionally comprises the steps of
(f) removing the liquid from the lower liquid receiving section, and
(g) cleaning the lower liquid receiving section.

Preferably, the pharmaceutical dosage form is an oral, mucosal, buccal, top-lingual, sub-lingual, topical, vaginal or rectal dosage form. The pharmaceutical dosage form is more preferably an orodispersible film.

Especially with orodispersible films, previous standard tests for measuring the disintegration time are prone to errors, due to, among other factors, the stickiness and fast disintegration of the orodispersible film. Therefore, the current method provides more reliable results.

The present invention also relates to a pharmaceutical dosage form characterized by a disintegration time of less than 10 minutes, preferably less than 5 minutes, more preferably less than 2 minutes, wherein the disintegration time is determined by the above-described method according to the invention.

The disintegration testing device according to the second aspect of the present invention comprises
(i) an upper liquid receiving section having a bottom side opening,
(ii) a lower liquid receiving section having a top side opening,
wherein the bottom side opening of the upper liquid receiving section and the top side opening of the lower liquid receiving section are formed so as to hold a pharmaceutical dosage form between the upper liquid receiving section and the lower liquid receiving section.

In the disintegration testing device according to the present invention, the upper liquid receiving section and the pharmaceutical dosage form are preferably attached tightly so as to form a liquid receptacle. In particular, the pharmaceutical dosage form constitutes the bottom of the upper liquid receiving section and at the same time the top cover of the lower liquid receiving section in the disintegration testing device according to the present invention.

In the disintegration testing device according to the present invention, the rim of the bottom side opening of the upper liquid receiving section and the rim of the top side opening of the lower liquid receiving section preferably each have a planar surface. More preferably, the rim of the bottom side opening of the upper liquid receiving section and the rim of the top side opening of the lower liquid receiving section each form complementary parts of a ground joint.

The upper liquid receiving section of the disintegration testing device according to the present invention can be made of glass or a transparent plastic material. The lower liquid receiving section of the disintegration testing device according to the present invention can be made of glass or a transparent plastic material. Preferably, both the upper liquid receiving section and the lower liquid receiving section of the disintegration testing device according to the present invention are made of glass. In an alternative preferred aspect, both the upper liquid receiving section and the lower liquid receiving section of the disintegration testing device according to the present invention are made of a transparent plastic material.

In another preferred aspect, the upper liquid receiving section and the lower liquid receiving section of the disintegration testing device according to the present invention are made of glass and the rim of the bottom side opening of the upper liquid receiving section and the rim of the top side opening of the lower liquid receiving section each form complementary parts of a ground joint.

In a further preferred aspect, the bottom side opening of the upper liquid receiving section and the top side opening of the lower liquid receiving section of the disintegration testing device according to the present invention have approximately the same size. "Approximately the same size" means that the surface area of the bottom side opening of the upper liquid receiving section is 0 to 20%, preferably 0 to 10%, more preferably 0 to 5%, smaller or bigger compared to the surface area of the top side opening of the lower liquid receiving section. In an even more preferred aspect, the bottom side opening of the upper liquid receiving section and the top side opening of the lower liquid receiving section of the disintegration testing device according to the present invention have the same size.

In a further preferred aspect, the bottom side opening of the upper liquid receiving section and the top side opening of the lower liquid receiving section of the disintegration testing device according to the present invention have approximately the same size and the rim of the bottom side opening of the upper liquid receiving section and the rim of the top side opening of the lower liquid receiving section each form complementary parts of a ground joint.

In a particularly preferred aspect, the upper liquid receiving section and the lower liquid receiving section of the disintegration testing device according to the present invention are made of glass, the rim of the bottom side opening of the upper liquid receiving section and the rim of the top side opening of the lower liquid receiving section each form complementary parts of a ground joint, and the bottom side opening of the upper liquid receiving section and the top side opening of the lower liquid receiving section of the disintegration testing device according to the present invention have approximately the same size.

The upper liquid receiving section of the disintegration testing device according to the present invention preferably has a cylindrical, cuboid or prismatic form, more preferably a cylindrical form. Furthermore, the lower liquid receiving section of the disintegration testing device according to the present invention preferably has a cylindrical, cuboid or prismatic form, more preferably a cylindrical form. In a particularly preferred aspect, both the upper liquid receiving section and the lower liquid receiving section of the disintegration testing device according to the present invention have a cylindrical form. In a further preferred aspect, both the upper liquid receiving section and the lower liquid receiving section of the disintegration testing device according to the present invention have a cylindrical form and the pharmaceutical dosage form constitutes the bottom of the cylindrical upper liquid receiving section and at the same time the top cover of the cylindrical lower liquid receiving section. In a further preferred aspect, both the upper liquid receiving section and the lower liquid receiving section of the disintegration testing device according to the present invention have a cylindrical form, the bottom side opening of the upper liquid receiving section and the top side opening of the lower liquid receiving section have approximately the same size, and the pharmaceutical dosage form constitutes the bottom of the cylindrical upper liquid receiving section and at the same time the top cover of the cylindrical lower liquid receiving section. Cylindrical forms with a round upper or lower surface area are preferred, because they provide for a quicker and easier arrangement of the upper liquid receiving section and the lower liquid receiving section compared to other forms.

The disintegration testing device according to the present invention may further comprise a liquid delivery means arranged so as to deliver a liquid to the upper side of the pharmaceutical dosage form. The liquid delivery means is preferably a dosing device allowing for delivery of a constant amount of liquid, for example a liquid dispenser provided with a valve or a pipette, or a semi-automatic or automatic device, for example, a pump, an electromagnetic shutter device or an automated liquid handling device, such as an automated liquid handling device which is commercially available, for example, from Eppendorf or Hamilton Robotics. The liquid delivery means can be arranged above or within the upper liquid receiving section.

The upper liquid receiving section of the disintegration testing device according to the present invention may comprise gradations allowing to determine the volume of the liquid received by the upper liquid receiving section.

The disintegration testing device of the present invention may further comprise a detecting means for detecting the liquid penetration through the pharmaceutical dosage form. The detecting means is preferably arranged below the top side opening of the lower liquid receiving section. The detecting means is preferably an electronic measurement device, such as: a weight change sensor (preferably an electronic balance), an impact sensor, an image recognition sensor (preferably a photo sensor), a capacitive sensor, an electric resistivity sensor, a motion sensor, a vibration sensor, and an acoustic sensor. The detecting means can be arranged on, in or outside the wall and/or on, in or outside the bottom of the lower liquid receiving section or within the lower liquid receiving section. Using electronic measurement devices further improves standardizing the time measurement to afford a reproducible and sensitive measurement, in particular for long duration and short duration events.

The disintegration testing device according to the present invention preferably further comprises a time measuring means. The time measuring means is preferably adapted to measure the time between
- placing the liquid into the upper liquid receiving section and
- the liquid penetration through the pharmaceutical dosage form, but more preferably the moment of detachment and fall of a first droplet from the pharmaceutical dosage form.

In the disintegration testing device according to the present invention, the time measurement means is preferably coupled to the detecting means or the liquid delivery means. More preferably, the time measurement means is coupled to the liquid delivery means and the detecting means.

The disintegration testing device according to the present invention preferably further comprises a temperature adjustment means. In one preferred aspect, the temperature adjustment means may be a vessel containing a temperature control medium surrounding at least a part of the disintegration testing device as defined above.

In a further preferred aspect, the temperature adjustment means of the disintegration testing device according to the present invention comprises an outer wall surrounding the inner wall of the upper liquid receiving section, said outer wall having at least one opening for inserting and withdrawing a temperature control medium. In an alternative preferred aspect, the temperature adjustment means of the disintegration testing device according to the present invention comprises an outer wall surrounding the inner wall of the upper liquid receiving section, said outer wall has two openings, one inlet for inserting the temperature control medium and one outlet for withdrawing the temperature control medium. The outer wall surrounding the inner wall of the upper liquid receiving section may include or exclude the rim of the bottom side opening of the upper liquid receiving section. In the disintegration testing device according to the present invention, the temperature control medium is preferably circulated between the inner and outer walls.

In the disintegration testing device according to the present invention, the temperature adjustment means preferably also comprises an outer wall surrounding the inner wall of the upper liquid receiving section and an outer wall surrounding the inner wall of the lower liquid receiving section, wherein each of said outer walls have at least one opening for inserting and withdrawing the temperature control medium. In the disintegration testing device according to the present invention, the temperature adjustment means preferably also comprises an outer wall surrounding the inner wall of the upper liquid receiving section and an outer wall surrounding the inner wall of the lower liquid receiving section, wherein each of said outer walls have two openings, one inlet for inserting the temperature control medium and one outlet for withdrawing the temperature control medium. The outer walls surrounding the inner walls of the upper liquid receiving section and the lower liquid receiving section preferably include or exclude the rim of the bottom side opening of the upper liquid receiving section and the rim of the top side opening of the lower liquid receiving section. In the disintegration testing device according to the present invention, the temperature control medium is preferably circulated between the inner and outer walls.

The temperature-adjustment means of the disintegration testing device according to the present invention preferably additionally comprises a means for adjusting the temperature of the liquid delivery means.

The temperature control medium which is preferably used in the disintegration testing device according to the present invention is a heating liquid or a cooling liquid. The temperature control medium can be selected from water, an organic solvent or a mixture of water and an organic solvent.

In the disintegration testing device according to the present invention, the size of the bottom side opening of the upper liquid receiving section and the size of the top side opening of the lower liquid receiving section are preferably adapted to the size of the film-shaped pharmaceutical dosage form. "Adapted" means that the bottom side opening of the upper liquid receiving section and the top side opening of the lower liquid receiving section have a size which is only as much smaller compared to the film-shaped pharmaceutical dosage form as it is necessary for securely holding the film-shaped pharmaceutical dosage form between the upper liquid receiving section and the lower liquid receiving section. In other words, preferably a maximum area of the film-shaped pharmaceutical dosage form constitutes the bottom of the upper liquid receiving section and at the same time the top cover of the lower liquid receiving section. Thus, a maximum area of the film-shaped pharmaceutical dosage form is contacted by the liquid applied to the upper liquid receiving section. Preferably, the bottom side opening of the upper liquid receiving section and the top side opening of the lower liquid receiving section each have a surface area of at least 70%, more preferably at least 80%, even more preferably at least 90% of the surface area of the film-shaped pharmaceutical dosage form. However, in general the bottom side opening of the upper liquid receiving section and the top side opening of the lower liquid receiving section each preferably have a surface area of about 10 to 90%, preferably 20 to 90%, more preferably 30 to 90%, compared to the surface area of the pharmaceutical dosage form.

In the disintegration testing device according to the present invention, the bottom side opening of the upper liquid receiving section and the top side opening of the lower liquid receiving section have, preferably, a circular, ellipsoid, rectangular, square or polygonal (such as hexagonal) shape, more preferably a circular shape. More preferably, the bottom side opening of the upper liquid receiving section and the top side opening of the lower liquid receiving section are circular and have approximately the same size. Even more preferably, the bottom side opening of the upper liquid receiving section and the top side opening of the lower liquid receiving section are circular, have approximately the same size and are adapted to the size of the pharmaceutical dosage form such that the bottom side opening of the upper liquid receiving section and the top side opening of the lower liquid receiving section each have a surface area being about 10 to 90%, preferably 20 to 90%, more preferably 30 to 90%, smaller than the surface area of the pharmaceutical dosage form.

For example, the film-shaped pharmaceutical dosage form may have a size of from 0.1 to 10 cm$^2$, preferably 0.25 to 8 cm$^2$, more preferably 1 to 6 cm$^2$.

In the disintegration testing device according to the present invention, the film-shaped pharmaceutical dosage form is preferably attached between the upper liquid receiving section and the lower liquid receiving section with a fixing device. The fixing device can, preferably, be selected from the group consisting of a clamp, clip, bracket, spring and/or vice.

The lower liquid receiving section of the disintegration testing device according to the present invention preferably comprises a pressure balance opening connecting the inner part of the lower liquid receiving section (the part surrounded by the lower liquid receiving section itself and the film-shaped pharmaceutical dosage form as a top cover) with the environment outside the disintegration testing device. The pressure balance opening ensures the absence of any undesired pressure differences between the upper liquid receiving section and the lower liquid receiving section.

The disintegration testing device according to the present invention can preferably be connected to a data recording and storage system, the system recording the time between
- placing the liquid into the upper liquid receiving section and
- the liquid penetration through the pharmaceutical dosage form, but more preferably the moment of detachment and fall of a first droplet from the pharmaceutical dosage form.

In a preferred variant, the data recording and storage system further records the temperature as adjusted by the temperature adjustment means.

In a particularly preferred aspect of the present invention, the disintegration testing device is a completely automatically working device, wherein the liquid is automatically applied into the upper liquid receiving section and thus onto the upper side of the film-shaped pharmaceutical dosage form by an automatic liquid delivery means, the penetration of the liquid through the film-shaped pharmaceutical dosage form is detected by an automatic detecting means, the time between the application of the liquid into the upper liquid receiving section and the penetration of the liquid through the film-shaped pharmaceutical dosage form is automatically measured by an automatic time measuring means, and the measured time is automatically recorded by a data recording and storage system.

In a third aspect, the present invention relates to the use of a device comprising
(i) an upper liquid receiving section having a bottom side opening,
(ii) a lower liquid receiving section having a top side opening, wherein the bottom side opening of the upper liquid receiving section and the top side opening of the lower liquid receiving section being formed so as to hold a film-shaped pharmaceutical dosage form between the upper liquid receiving section and the lower liquid receiving section
for determining the disintegration time of the film-shaped pharmaceutical dosage form. The pharmaceutical dosage form is preferably an orodispersible film. The device may be characterized by the preferred features and aspects as described above for the second aspect of the present invention.

The present invention further relates to a film-shaped pharmaceutical dosage form, characterized by a disintegration time of less than 10 minutes, preferably less than 5 minutes, more preferably less than 2 minutes, wherein the disintegration time is determined by using the device according to the second aspect of the present invention. The pharmaceutical dosage form is preferably an oral, mucosal, buccal, top-lingual, sub-lingual, topical, vaginal or rectal dosage form. The pharmaceutical dosage form is more preferably an orodispersible film.

The following figures illustrate specific embodiments of the present invention and should not be construed to limit the scope of the invention as indicated by the appended claims in any way.

FIG. 2a shows a sectional view of a third embodiment of a disintegration testing device according to the invention;

FIGS. 6 to 11 show the disintegration behavior as observed in Comparative Example 1a.

Figure 1:
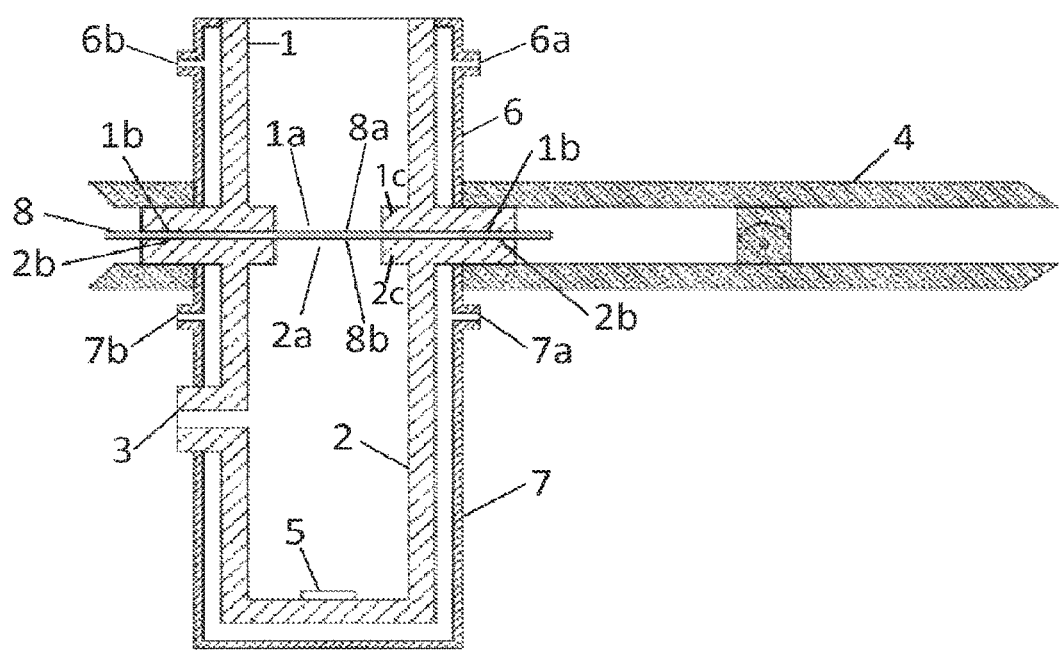
FIG. 1 shows a sectional view of a first embodiment of a disintegration testing device according to the invention.

FIG. 1 illustrates an example of a disintegration testing device according to the present invention. The device comprises an upper liquid receiving section 1 having a bottom side opening 1a and a lower liquid receiving section 2 having a top side opening 2a. The pharmaceutical dosage form 8 is placed between the upper liquid receiving section 1 and the lower liquid receiving section 2.

The bottom side opening 1a of the upper liquid receiving section 1 and the top side opening 2a of the lower liquid receiving section 2 are in axial alignment with each other.

The bottom side opening 1a of the upper liquid receiving section 1 has the same shape and size as the top side opening 2a of the lower liquid receiving section 2.

In a preferred embodiment, the rim 1b of the bottom side opening 1a of the upper liquid receiving section 1 and the rim 2b of the top side opening 2a of the lower liquid receiving section 2 are each complementary parts of a ground joint. As shown in FIG. 1, the rims 1b, 2b preferably project inwardly from the sides of the upper and lower receiving sections 1,2, forming projections 1c, 2c that partially cover or restrict the openings 1a, 2a.

The lower liquid receiving section 2 may have a pressure balance opening 3.

The upper liquid receiving section 1, the lower liquid receiving section 2 and the film-shaped pharmaceutical dosage form 8 placed between them may be fixed together with a clamp 4.

At the bottom of the lower liquid receiving section 2, a detecting means 5 may be provided (for example an electrical resistance sensor for detecting a droplet impact).

In a preferred embodiment, a temperature adjustment means 6 surrounding the upper liquid receiving section 1 is provided. The temperature adjustment means 6 has two openings 6a and 6b, 6a being the inlet for inserting the temperature control medium and 6b being the outlet for withdrawing the temperature control medium. Additionally, a temperature adjustment means 7 surrounding the lower liquid receiving section 2 is provided. The temperature adjustment means 7 has two openings 7a and 7b, 7a being the inlet for inserting the temperature control medium and 7b being the outlet for withdrawing the temperature control medium.

When determining the disintegration time of a film-shaped pharmaceutical dosage form 8, the liquid applied into the upper liquid receiving section 1 and thus onto the upper side of the film-shaped pharmaceutical dosage form 8a penetrates through the pharmaceutical dosage form 8. A droplet is formed at the bottom side 8b of the pharmaceutical dosage form 8 (the side representing the top cover of the lower liquid receiving section 2). The droplet eventually detaches from the pharmaceutical dosage form 8 and falls down into the lower liquid receiving section 2. This point in time is detected by visual observation or by detecting of the droplet fall by a detecting means 5, for example an electric resistivity sensor placed at the bottom of the lower liquid receiving section 2 and/or by a photo sensor (not shown in FIG. 1) placed outside the lower liquid receiving section 2.

Figure 2:
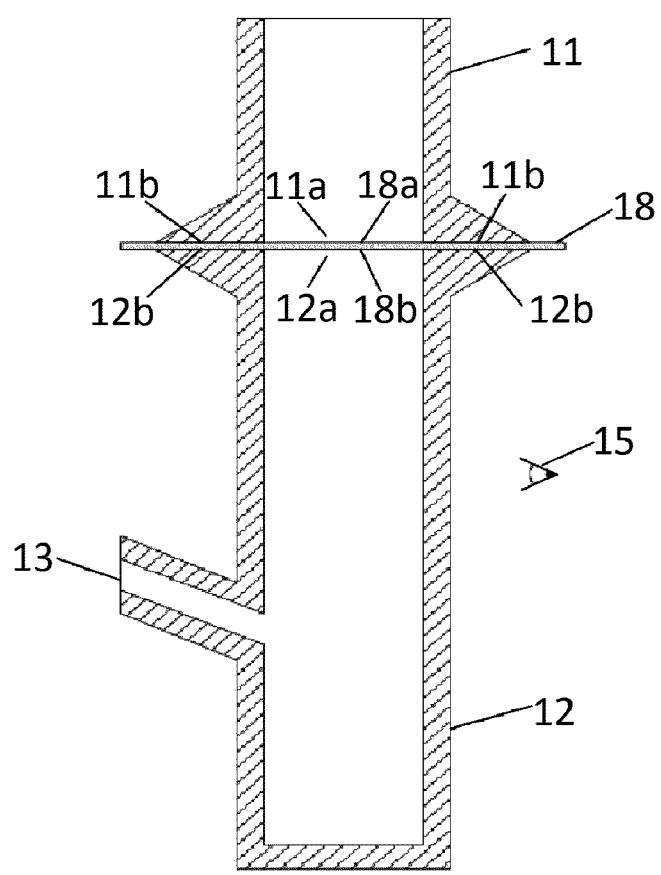
FIG. 2 shows a sectional view of a second embodiment of a disintegration testing device according to the invention.

A second embodiment of the disintegration testing device according to the invention is shown in FIG. 2

The device comprises an upper liquid receiving section 11 having a bottom side opening 11a and a lower liquid receiving section 12 having a top side opening 12a. The pharmaceutical dosage form 18 is placed between the upper liquid receiving section 11 and the lower liquid receiving section 12.

The bottom side opening 11a of the upper liquid receiving section 11 and the top side opening 12a of the lower liquid receiving section 12 are brought into axial alignment with each other.

The bottom side opening 11a of the upper liquid receiving section 11 has a cylindrical shape. The top side opening 12a of the lower liquid receiving section 12 also has a cylindrical shape. The diameter of the bottom side opening 11a is identical to the diameter of the top side opening 12a.

In a preferred embodiment, the rim 11b of the bottom side opening 11a of the upper liquid receiving section 11 and the rim 12b of the top side opening 12a of the lower liquid receiving section 12 are each complementary parts of a ground joint.

The lower liquid receiving section 12 may have a pressure balance opening 13.

Outside the lower liquid receiving section 12, a detecting means 15 may be provided (for example a photo sensor for detecting the droplet fall).

When determining the disintegration time of a film-shaped pharmaceutical dosage form 18, the liquid applied into the upper liquid receiving section 11 and thus onto the upper side of the pharmaceutical dosage form 18a penetrates through the pharmaceutical dosage form 18. A droplet is formed at the bottom side 18b of the pharmaceutical dosage form 18 (the side representing the top cover of the lower liquid receiving section 12). The droplet eventually detaches from the pharmaceutical dosage form 18 and falls down into the lower liquid receiving section 12. This point in time is detected by visual observation or by detection of the droplet fall by a detecting means 15, for example a photo sensor placed outside the lower liquid receiving section 12.

The third embodiment shown in FIG. 2a differs from the second embodiment of FIG. 2 in that the upper liquid receiving section 11, the lower liquid receiving section 12 and the film-shaped pharmaceutical dosage form 18 placed between them are fixed together with a clamp 14 and the detecting means 15 is not present (the droplet fall is detected by visual observation).

Figure 3:
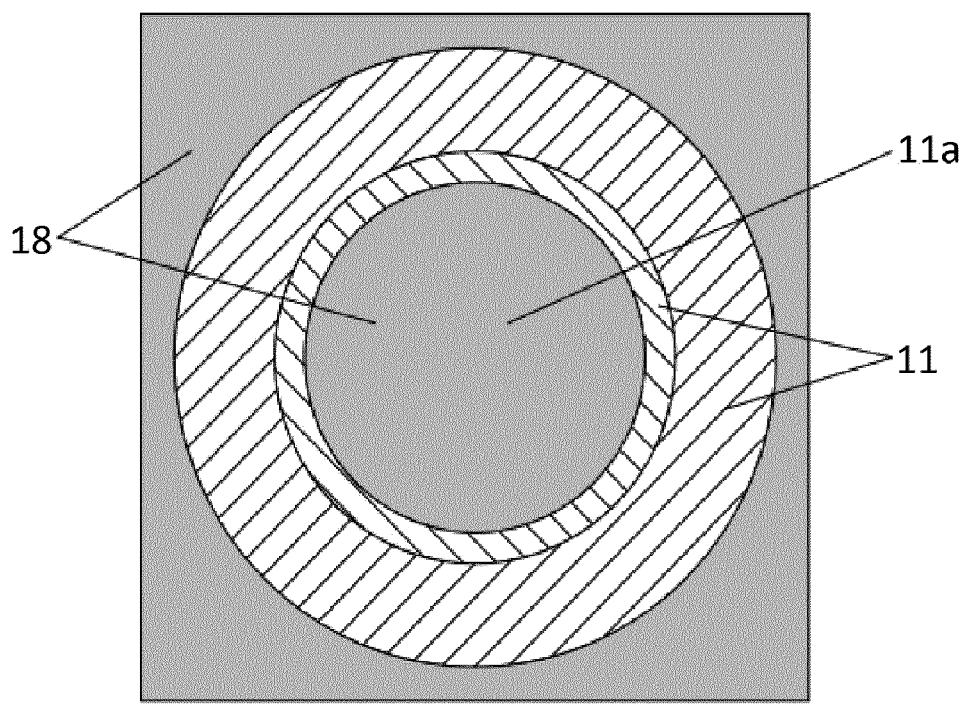
FIG. 3 shows a top view of the second embodiment of a disintegration testing device according to the invention.

FIG. 3 is a top view of the second embodiment of a disintegration testing device according to the invention as shown in FIG. 2 illustrating the cylindrical form of the upper liquid receiving section 11 and the bottom side opening 11a. FIG. 3 also illustrates an example of a square shaped pharmaceutical dosage form 18 which is, preferably, an orodispersible film.

Figure 4:
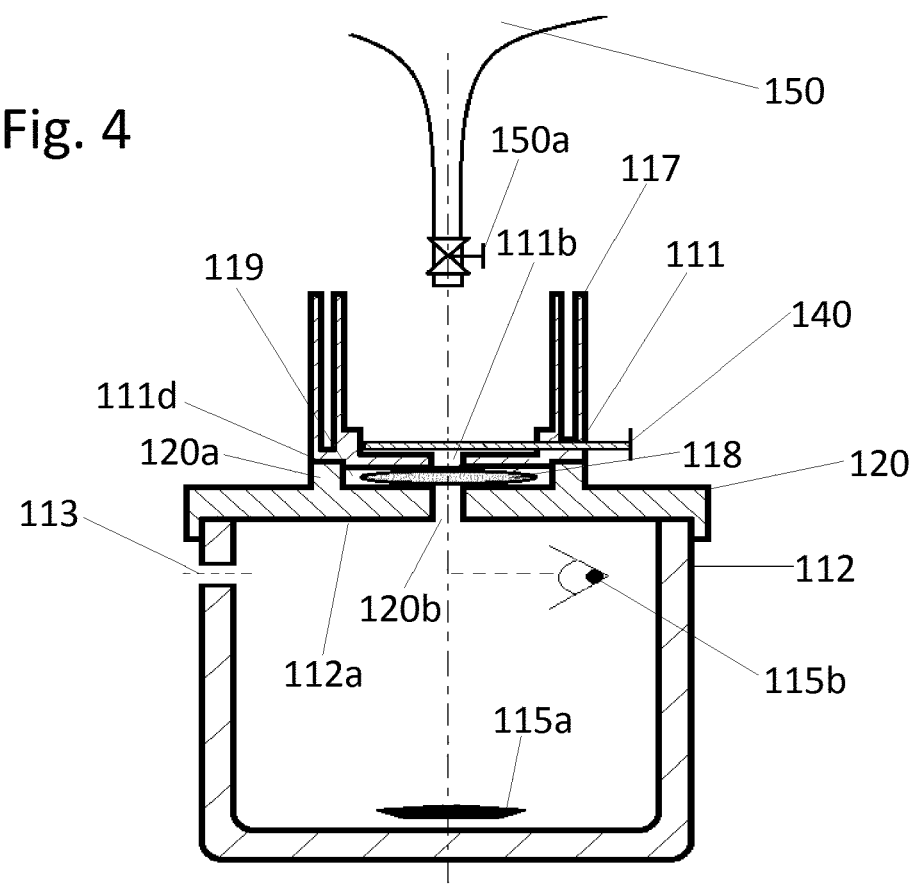
FIG. 4 shows a sectional view of a fourth embodiment of a disintegration testing device according to the invention.

A fourth embodiment of a disintegration testing device according to the invention shown in FIG. 4 comprises a cylindrical upper liquid receiving section 111 and cylindrical lower liquid receiving section 112. At the bottom of the lower liquid receiving section 112 there is provided an electrical resistance sensor 115a for detecting a droplet impact. Additionally or alternatively, a photo sensor 115b is attached on the inner side, in the wall or (in case of a transparent lower liquid receiving section 112) on the outer side (not shown) of the lower liquid receiving section 112. A pressure balance opening 113 can be provided in the side wall of the lower liquid receiving section 112.

A cover 120 comprising an upstanding flange 120a surrounding a through hole 120b, the axis of which intersects the axis of the photo sensor 115a, is fitted onto the top side opening 112a of the lower liquid receiving section.

A double walled upper liquid receiving section 111 is fitted into the upstanding flange 120a such that the bottom side opening 111b of the upper liquid receiving section 111 is axially aligned with and has the same diameter as the through hole 120b of the cover 120. Further, near the bottom of the upper liquid receiving section 111, a liquid tight slider valve 140 is provided which prevents liquid poured into the upper liquid receiving section 111 reaching the bottom side opening 111b and leaking out of the upper liquid receiving section 111. When the upper liquid receiving section 111 is fitted to the cover 120 as shown in FIG. 4, a bottom shoulder 111d comes to rest on the flange 120a, so that a gap 119 is formed between the bottom surface of the upper liquid receiving section 111 and the upper surface of the cover 120, said gap having exactly the same size (height) or a slightly smaller size (height) compared to the thickness (height) of the pharmaceutical dosage form 118 which is to be tested by the disintegration testing device. A liquid delivery means 150 is arranged above the upper liquid receiving section 111 and is provided with a valve 150a as a part of the liquid delivery means of the device according to the invention. The upper liquid receiving section 111 is double walled allowing the regulation of the liquid temperature after delivery (the outer wall thus constituting a temperature adjustment means 117).

In use, the upper liquid receiving section 111 of the disintegration testing device is removed from the cover 120 and a pharmaceutical dosage form 118 is placed into the cover 120 such as to close the through-hole 120b. Then the upper liquid receiving section 111 is fitted back into the flange 120a of the cover 120, thus tightly pressing the dosage form 118 against the cover 120 by its mere weight, so as to tightly close the liquid passage formed by the aligned through-hole 120b and bottom side opening 111b. Next, the test liquid is introduced from the liquid delivery means 150 into the upper liquid receiving section 111 by opening and then closing the valve 150a, while the slider valve 140 still remains closed. Once the desired volume of test liquid has been placed into the upper liquid receiving section 111, the slider valve 140 is pulled out to allow the liquid to flow through the bottom side opening 111b, thus coming into contact with the pharmaceutical dosage form 118. Time measurement starts when the slider valve 140 is pulled out. The test liquid penetrates the pharmaceutical dosage form and eventually forms a droplet below the dosage form. The fall of this droplet can be registered by the electrical resistance sensor 115a and/or the photo sensor 115b and/or by visual observation.

Figure 5:
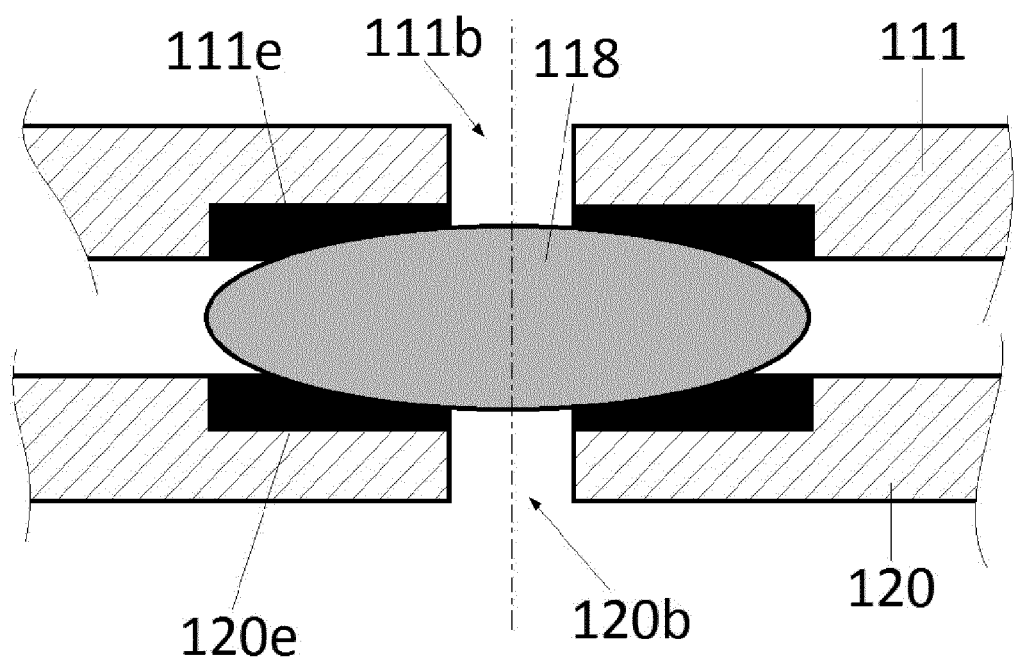
FIG. 5 shows a preferred aspect of the fourth embodiment of a disintegration testing device according to the invention.

FIG. 5 shows a preferred variant of the fourth embodiment of a disintegration testing device according to the invention. FIG. 5 only illustrates the relevant part of that preferred variant. The disintegration testing device comprises all the features of the device according to the fourth embodiment shown in FIG. 4 while providing in addition two dish rubber pads 111e and 120e forming the compression edges of the bottom side opening 111b of the upper liquid receiving section 111 and the through hole 120b of the cover 120, respectively. By means of this additional feature the fixation of a non-flat pharmaceutical dosage form 118 (such as an oblong tablet) can be improved.

Figure 5A:
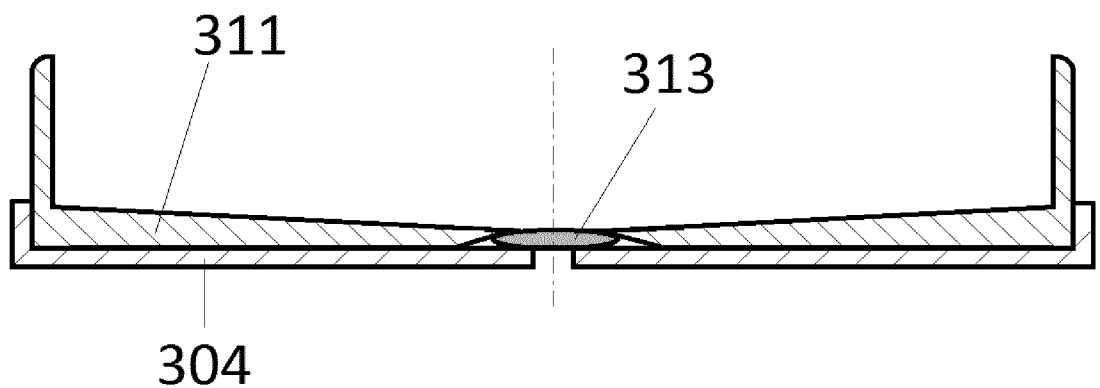
FIG. 5a shows an alternative preferred variant of the fourth embodiment of a disintegration testing device according to the invention.
Figure 6:
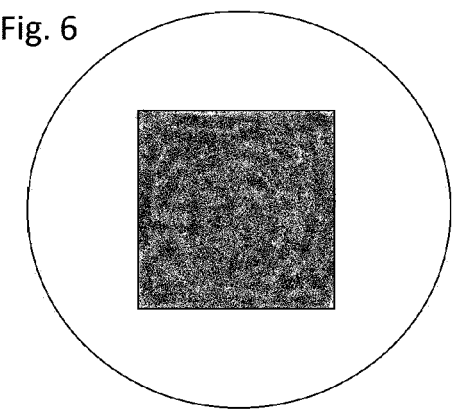
Figure 7:
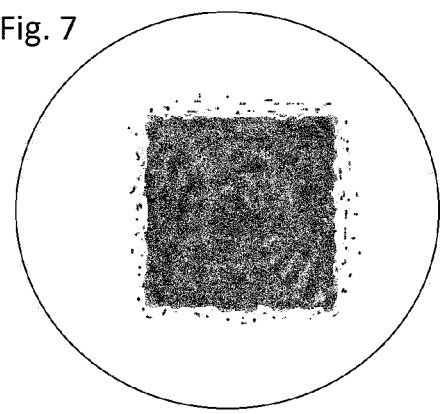
Figure 8:
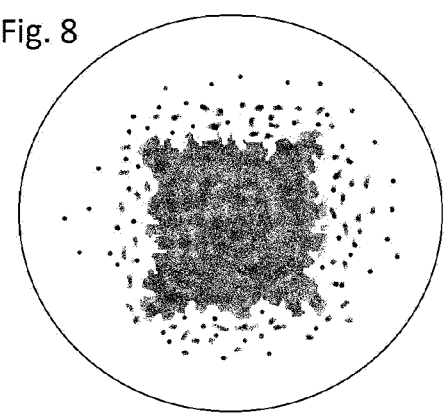
Figure 9:
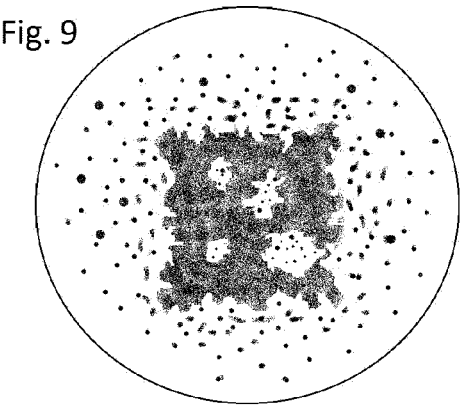
Figure 10:
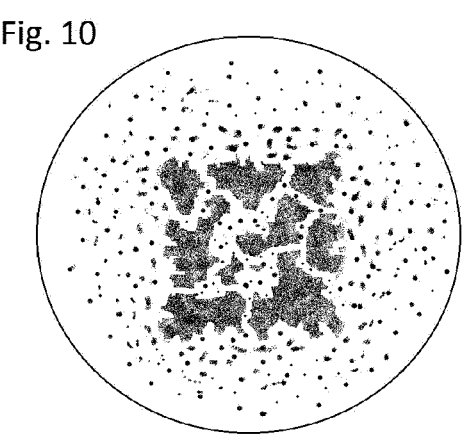
Figure 11:
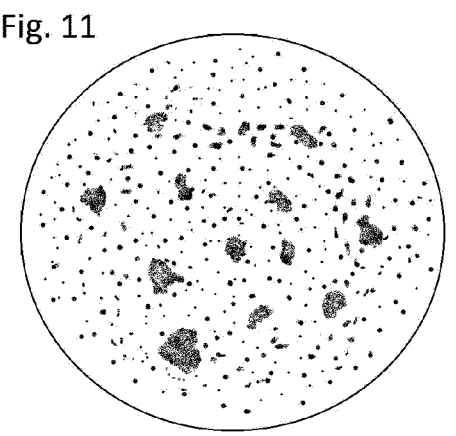

FIG. 5a shows an alternative preferred aspect of the fourth embodiment of a disintegration testing device according to the invention. FIG. 5a only illustrates the relevant part of that preferred aspect. The disintegration testing device comprises all the features of the device according to the fourth embodiment shown in FIG. 4, except that cover 120 is replaced by an alternative cover 304 and the upper liquid receiving section 111 is replaced by upper liquid receiving section 311, wherein the bottom side opening is shaped in a specific way as shown in FIG. 5a for fixation of a non-flat pharmaceutical dosage form 313 (such as an oblong tablet). Preferably, the bottom side opening of the upper liquid receiving section forms a lower crevice at the compression edges of the bottom side opening for flushly engaging and fixing the non-flat pharmaceutical dosage form, preferably in a form-fit manner.

The following examples merely illustrate the present invention and should not be construed to limit the scope of the invention as indicated by the appended claims in any way.

EXAMPLE 1

Orodispersible films containing 50 mg sildenafil citrate as active ingredient having a thickness of 162±10 μm and a surface area of 7 cm² were produced by preparing a suspension containing sildenafil citrate, polymers and further excipients, casting the suspension onto a support liner, drying the casted suspension to obtain a laminate, cutting the laminate into squares of 7 cm², removing the support liner and packaging each single orodispersible film into a sachet.

The disintegration time of orodispersible films obtained from the same suspension and laminate (from the same batch) was determined with a disintegration testing device as shown in FIG. 2a. The device was made of glass and had a cylindrical shape. The upper liquid receiving section had a volume of about 3 ml. The lower liquid receiving section had a volume of about 20 ml. The rim of the bottom side opening of the upper liquid receiving section and the rim of the top side opening of the lower liquid receiving section each formed as complementary parts of a ground joint. The circular bottom side opening of the upper liquid receiving section and the circular top side opening of the lower liquid receiving section each had a size of 1 cm². The lower liquid receiving section had a pressure balance opening.

Each orodispersible film was carefully taken out of the sachet with a pair of tweezers and placed centrally onto the top side opening of the lower liquid receiving section. The upper liquid receiving section was placed onto the orodispersible film while aligning its bottom side opening with the top side opening of the lower liquid receiving section. The upper liquid receiving section and the lower liquid receiving section were fixed together with a clamp. The visual integrity of the test area was checked.

Demineralized water having a temperature of 22° C. was used as test liquid. A micropipette was used to apply 250 μl of the test liquid into the upper liquid receiving section. Time measurement was started at the moment the liquid was pushed out of the micropipette. A calibrated stopwatch was used for time measurement. The fall of the first droplet was observed visually. Time measurement was terminated at the moment the droplet detached from the orodispersible film and fell down.

The results for the disintegration time are shown in the below table:

| Laboratory technician no. | Disintegration time [min] (mean values of 6 measurements) |
| --- | --- |
| 1 | 1.38 |
| 2 | 1.65 |
| 3 | 1.65 |
| 4 | 1.31 |
| 5 | 1.46 |
| 6 | 1.67 |

The relative standard deviation is 10.4%.

COMPARATIVE EXAMPLE 1a

The disintegration time of orodispersible films obtained from the same suspension and laminate (from the same batch) as in Example 1 was determined according to a prior art method as described below.

A Petri dish having an inner diameter of 5.5 cm was filled with 4 ml of demineralized water having a temperature of 22° C. Each orodispersible film was carefully taken out of the sachet with a pair of tweezers and placed centrally onto the water surface. Time measurement was started at the moment the orodispersible film came into contact with the water surface. A calibrated stopwatch was used for time measurement. The disintegration of the film-shaped pharmaceutical dosage form was then observed visually.

The orodispersible film started to disintegrate at some of the corners and edges; disintegration at other corners and edges followed. The film then became porous to a different extent at various parts of the film. Then, the porous structure fell apart and the single parts became smaller and moved away from each other. It was rather difficult to select a point in time representing the end-point of disintegration. The disintegration behavior is illustrated in FIGS. 6 to 11.

The results for the disintegration time are shown in the below table:

| Laboratory technician no. | Disintegration time [min] (mean values of 6 measurements) |
| --- | --- |
| 1 | 1.97 |
| 2 | 2.67 |
| 3 | 2.77 |
| 4 | 2.52 |
| 5 | 3.49 |
| 6 | 3.02 |

The relative standard deviation is 18.6%.

COMPARATIVE EXAMPLE 1b

An attempt was made to determine the disintegration time of orodispersible films obtained from the same suspension and laminate (from the same batch) as in Example 1 using the device according to the European Pharmacopeia (Ph. Eur. 8.0; Chapter 2.9.1, Test B). However, the first problem in determining the disintegration time arose from the definition of disintegration as made by the European Pharmacopeia. The orodispersible films to be analysed did not have a firm core before the disintegration test started. Therefore, the absence of such a firm core could not be used as a criterion for disintegration. Additionally, it was not possible to determine the disintegration time, because the orodispersible films stuck to the discs of the apparatus according to the European Pharmacopeia, thus hindering disintegration.

EXAMPLE 2

Orodispersible films containing 8 mg buprenorphine hydrochloride and 2 mg naloxone hydrochloride as active ingredients and having a thickness of 135±10 µm and a surface area of 2.9 cm$^2$ were produced by preparing a suspension containing the active ingredients, polymers and further excipients, casting the suspension onto a support liner, drying the cast suspension to obtain a laminate, cutting the laminate into squares of 2.9 cm$^2$, removing the support liner and packaging each single orodispersible film into a sachet.

The disintegration time of orodispersible films obtained from the same suspension and laminate (from the same batch) was determined with a disintegration testing device as shown in FIG. 2a. The device was made of glass and had a cylindrical shape. The upper liquid receiving section had a volume of about 1.5 ml. The lower liquid receiving section had a volume of about 10 ml. The rim of the bottom side opening of the upper liquid receiving section and the rim of the top side opening of the lower liquid receiving section each formed as complementary parts of a ground joint. The circular bottom side opening of the upper liquid receiving section and the circular top side opening of the lower liquid receiving section each had a size of 0.64 cm$^2$. The lower liquid receiving section had a pressure balance opening.

The orodispersible film was carefully taken out of the sachet with a pair of tweezers and placed onto the top side opening of the lower liquid receiving section centrally. The upper liquid receiving section was placed onto the orodispersible film while aligning its bottom side opening with the top side opening of the lower liquid receiving section. The upper liquid receiving section and the lower liquid receiving section were fixed together with a clamp. The visual integrity of the test area was checked.

Demineralized water having a temperature of 22° C. was used as test liquid. A micropipette was used to apply 200 µl of the test liquid into the upper liquid receiving section. Time measurement was started at the moment the liquid was pushed out of the micropipette. A calibrated stopwatch was used for time measurement. The fall of the first droplet was observed visually. Time measurement was terminated at the moment the droplet detached from the orodispersible film and fell down.

The results for the disintegration time are shown in the below table:

| Laboratory technician no. | Disintegration time [min] (single value of 1 measurement) |
|---|---|
| 1 | 2.86 |
| 1 | 2.73 |
| 1 | 2.90 |
| 1 | 2.51 |
| 1 | 2.85 |
| 1 | 2.75 |
| 1 | 2.58 |
| 2 | 2.47 |
| 2 | 3.27 |
| 2 | 3.65 |

The relative standard deviation overall is 12.7%.

COMPARATIVE EXAMPLE 2a

The disintegration time of orodispersible films obtained from the same suspension and laminate (from the same batch) as in Example 2 was determined according to a prior art method as described below.

A Petri dish having an inner diameter of 5 cm was filled with 2 ml of demineralized water having a temperature of 22° C. The orodispersible film was carefully taken out of the sachet with a pair of tweezers and placed centrally onto the water surface. Time measurement was started at the moment the orodispersible film came into contact with the water surface. A calibrated stopwatch was used for time measurement. The disintegration of the film-shaped pharmaceutical dosage form was then observed visually.

The orodispersible film started to disintegrate at some of the corners and edges, disintegration at other corners and edges followed. The film then became porous to a different extent at various parts of the film. Then, the porous structure fell apart, some parts stayed on the water surface, some parts sunk down. The parts that stayed on the water surface decomposed more slowly compared to the parts that had sunken down. It was rather difficult to select a point in time representing the end-point of disintegration.

The results for the disintegration time are shown in the below table:

| Laboratory technician no. | Disintegration time [min] (single value of 1 measurement) |
|---|---|
| 1 | 1.00 |
| 1 | 1.03 |
| 1 | 1.08 |
| 1 | 0.63 |
| 1 | 0.83 |
| 1 | 0.80 |
| 1 | 0.73 |
| 2 | 2.07 |
| 2 | 1.80 |
| 2 | 2.43 |

The relative standard deviation overall is 50.6%.

COMPARATIVE EXAMPLE 2b

An attempt was made to determine the disintegration time of orodispersible films obtained from the same suspension and laminate (from the same batch) as in Example 2 using the device according to the European Pharmacopeia (Ph. Eur. 8.0; Chapter 2.9.1, Test B). However, it was not possible to determine the disintegration time due to the same problems as described in Example 1b.

The invention claimed is:

1. A method for determining a disintegration time of a film-shaped pharmaceutical dosage form, the method comprising:
   (a) placing the film-shaped pharmaceutical dosage form horizontally between a bottom side opening of an upper liquid receiving section and a top side opening of a lower liquid receiving section such that the film-shaped pharmaceutical dosage form occludes the top side opening of the lower liquid receiving section and the bottom side opening of the upper liquid receiving section, wherein the bottom side opening and the top side opening are positioned and aligned such that, but for the presence of the intact film-shaped pharmaceutical dosage form, liquid would flow under gravity from the bottom side opening through the top side opening into the lower liquid receiving section;
   (b) applying a liquid into the upper liquid receiving section;
   (c) detecting a penetration of the liquid through the film-shaped pharmaceutical dosage form, wherein the penetration of the liquid through the film-shaped pharmaceutical dosage form occurs when a first droplet detaches from the film-shaped pharmaceutical dosage form to fall into the lower liquid receiving section; and
   (d) determining the time between step (b) and step (c).

2. The method according to claim 1, wherein the liquid is water or an artificial body fluid.

3. The method according to claim 2, wherein the artificial body fluid is one or more selected from the group consisting of artificial saliva, artificial gastric juice and artificial gut juice.

4. The method according to claim 1, wherein the penetration of the liquid through the film-shaped pharmaceutical dosage form is detected visually or by one or more detecting means selected from the group consisting of a weight change sensor, an impact sensor, an image recognition sensor, a capacitive sensor, an electric resistivity sensor, a motion sensor, a vibration sensor, and an acoustic sensor.

5. The method according to claim 1, wherein the time between step (b) and step (c) is measured manually or automatically with a time measurement means.

6. The method according to claim 1, wherein the time between step (b) and step (c) is measured by a time measurement means which is coupled
   to a liquid delivery means which applies the liquid into the upper liquid receiving section; or
   to a detecting means which detects the penetration of the liquid through the pharmaceutical dosage form; or
   to a liquid delivery means which applies the liquid into the upper liquid receiving section and a detecting means which detects the penetration of the liquid through the pharmaceutical dosage form.

7. The method according to claim 1, wherein the film-shaped pharmaceutical dosage form is an orodispersible film.

8. A disintegration testing device, that carries out the method according to claim 1, comprising
   (i) the upper liquid receiving section, having a bottom side opening, and
   (ii) the lower liquid receiving section, having a top side opening, wherein
   the bottom side opening of the upper liquid receiving section and the top side opening of the lower liquid receiving section are formed so as to hold the film-shaped pharmaceutical dosage form between the upper liquid receiving section and the lower liquid receiving section.

9. The disintegration testing device according to claim 8, wherein a rim of the bottom side opening of the upper liquid receiving section and a rim of the top side opening of the lower liquid receiving section each have a planar surface.

10. The disintegration testing device according to claim 8, wherein
    the upper liquid receiving section has a cylindrical form;
    the lower liquid receiving section has a cylindrical form;
    the film-shaped pharmaceutical dosage form constitutes the bottom of the cylindrical upper liquid receiving section and at the same time a top cover of the cylindrical lower liquid receiving section; and
    the bottom side opening of the upper liquid receiving section and the top side opening of the lower liquid receiving section have approximately the same size.

11. The disintegration testing device according to claim 8 further comprising
    a liquid delivery means arranged so as to deliver a liquid to an upper side of the film-shaped pharmaceutical dosage form.

12. The disintegration testing device according to claim 8 further comprising
    a detecting means for detecting the liquid penetration through the film-shaped pharmaceutical dosage form.

13. The disintegration testing device according to claim 12, wherein the detecting means is one or more detecting means selected from the group consisting of a weight change sensor, an impact sensor, an image recognition sensor, a capacitive sensor, an electric resistivity sensor, a motion sensor, a vibration sensor, and an acoustic sensor.

14. The disintegration testing device according to claim 8 further comprising
    a time measuring means.

15. The disintegration testing device according to claim 14, wherein the time measuring means is coupled to
    a detecting means for detecting the liquid penetration through the film-shaped pharmaceutical dosage form, or
    a liquid delivery means arranged so as to deliver a liquid to an upper side of the film-shaped pharmaceutical dosage form, or
    the detecting means and the liquid delivery means.

* * * * *